United States Patent
Hayashi et al.

(10) Patent No.: US 7,893,306 B2
(45) Date of Patent: Feb. 22, 2011

(54) PROCESS FOR PRODUCTION OF BIPHENYL DERIVATIVES

(75) Inventors: Tamio Hayashi, 12-8, Oogino-sato Higashi 7-chome, Otsu-shi, Shiga 520-0248 (JP); Jiro Nakatani, Moriyama (JP)

(73) Assignees: Toray Fine Chemicals Co., Ltd. (JP); Tamio Hayashi (JP)

( * ) Notice: Subject to any disclaimer, the term of this patent is extended or adjusted under 35 U.S.C. 154(b) by 362 days.

(21) Appl. No.: 12/092,466

(22) PCT Filed: Oct. 25, 2006

(86) PCT No.: PCT/JP2006/321305

§ 371 (c)(1),
(2), (4) Date: May 2, 2008

(87) PCT Pub. No.: WO2007/052516

PCT Pub. Date: May 10, 2007

(65) Prior Publication Data

US 2008/0319238 A1    Dec. 25, 2008

(30) Foreign Application Priority Data

Nov. 4, 2005    (JP) ............................. 2005-321405

(51) Int. Cl.
C07C 22/00 (2006.01)
C07C 19/08 (2006.01)
C07C 17/00 (2006.01)

(52) U.S. Cl. ...................... 570/184; 570/140; 570/143; 570/183; 570/190

(58) Field of Classification Search ................ 570/140, 570/144, 183, 190
See application file for complete search history.

(56) References Cited

U.S. PATENT DOCUMENTS

| | | | |
|---|---|---|---|
| 1,996,746 A | | 4/1935 | Briton et al. |
| 2,959,596 A | | 11/1960 | Ramsden et al. |

FOREIGN PATENT DOCUMENTS

| | | |
|---|---|---|
| JP | 63-295520 | 12/1988 |
| JP | 04-005248 A | 1/1992 |
| JP | 04-169542 A | 6/1992 |
| JP | 63-295520 | 12/1998 |
| JP | 2005-126330 | 5/2005 |
| WO | 2007-128601 | 11/2007 |

OTHER PUBLICATIONS

Krasovskiy, et al, "Transition-Metal-Free Homocoupling of Organomagnesium Compounds", *Angewandte Chemie, International Edition*, 2006, pp. 5010-5014.

S. Ravi Kanth et al. "AnBr$_2$—Catalyzed Efficient Oxidative Homo Coupling of Aryl Magnesium Bromides", *Synthetic Communications*, 2006, vol. 36, pp. 3079-3084.

Nagano, T. et al., "Iron-Catalyzed Oxidative Homo-coupling of Aryl Grignard Reagents," *Organic Letters*, 2005, vol. 7, No. 3; pp. 491-493.

Cahiez, G. et al., "Iron-Catalyzed Homo-Coupling of Simple and Functionalized Arylmagnesium Reagents," *Organic Letters*, 2005, vol. 7, No. 10, pp. 1943-1946.

Lourak et al., "Activation of Reducing Agents. Sodium Hydride Containing Complex Reducing Agents. 31. NiCRAL's as Very Efficient Agents in Promoting Homo-Coupling of Aryl Halides," *J. Org. Chem.*, vol. 54, 1989, pp. 4810-4844.

*Primary Examiner*—Jafar Parsa
(74) *Attorney, Agent, or Firm*—DLA Piper LLP (US)

(57) ABSTRACT

A process for producing biphenyl derivatives represented by formula (1), including reacting a chlorine atom of a benzene derivative represented by formula (2) with metallic magnesium to form a Grignard reagent, and coupling two molecules of the Grignard reagent with each other in the presence of a catalyst.

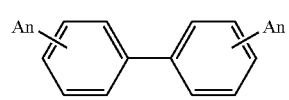

formula (1)

(wherein A represents at least one member selected from the group consisting of trifluoromethyl and fluoro, and n is an integer of 1 to 4.)

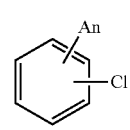

formula (2)

(wherein A represents at least one member selected from the group consisting of trifluoromethyl and fluoro, and n is an integer of 1 to 4.)

7 Claims, No Drawings

PROCESS FOR PRODUCTION OF BIPHENYL DERIVATIVES

RELATED APPLICATIONS

This is a §371 of International Application No. PCT/JP2006/321305, with an international filing date of Oct. 25, 2006 (WO 2007/052516 A1, published May 10, 2007), which is based on Japanese Patent Application No. 2005-321405, filed Nov. 4, 2005.

TECHNICAL FIELD

This disclosure relates to a process for the production of biphenyl derivatives, and more particularly, to a process for the production of biphenyl derivatives that are excellent in industrial productivity.

BACKGROUND

Biphenyl derivatives are compounds widely used in the fields of organic chemistry and polymer chemistry, being useful in industrial applications across a wide range of fields such as fine chemicals, pharmaceutical and agricultural raw materials, raw material for resins and plastics, electronic and information materials, and optical materials.

A process for the production of biphenyl derivatives is known wherein aromatic halides are used as the starting substrate. Japanese Patent Application Kokai Publication No. S63-295520 (Examples 1, 2, 3, 4) proposes a process wherein a Grignard reagent of aromatic chlorides and aromatic bromides are made to react in the presence of a nickel catalyst. At the same time, ORGANIC LETTERS, Vol. 7, No. 3 (2005), 491-493; and ORGANIC LETTERS, Vol. 7, No. 10 (2005), 1943-1946 propose a process wherein aromatic iodides or aromatic bromides are made to react with magnesium to form a Grignard reagent, and then two molecules of the Grignard reagent are coupled to each other using an iron chloride (III) catalyst in the presence of an oxidizing agent.

However, with the process described in Japanese Patent Application Kokai Publication No. S63-295520 (Examples 1, 2, 3, 4), the yield of biphenyl derivatives has been low in the case where the substrate that reacts with the Grignard reagent is an aromatic chloride, and thus the process has not been suitable for industrial use. In addition, with the production process described in ORGANIC LETTERS, Vol. 7, No. 3 (2005), 491-493 and ORGANIC LETTERS, Vol. 7, No. 10 (2005), 1943-1946, although the reactivity of the starting substrate is high, expensive aromatic iodides or aromatic bromides; are used, and for this reason the produced biphenyl derivatives have also become expensive.

It could therefore be advantageous to provide a process for the production of biphenyl derivatives that are excellent in industrial productivity by virtue of the use of inexpensive and easily available raw materials.

SUMMARY

We provide processes for the production of biphenyl derivatives. In the processes for the production of biphenyl derivatives represented by the following general formula (1), the chlorine atom of a benzene derivative represented by the following general formula (2) is made to react with metallic magnesium to form a Grignard reagent, and then two molecules of the Grignard reagent are coupled to each other in the presence of a catalyst.

General formula (1) is:

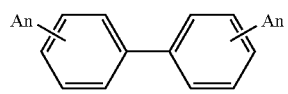

(wherein A represents at least one member selected from the group, consisting of trifluoromethyl and fluoro, and n is an integer of 1 to 4.)

General formula (2) is:

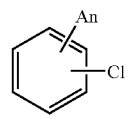

(wherein A represents at least one member selected from the group consisting of trifluoromethyl and fluoro, and n is an integer of 1 to 4.)

Since the process for the production of biphenyl derivatives uses inexpensive aromatic chlorides as the starting substrate, the Grignard reagent can be produced inexpensively as an intermediate. Then, by coupling two molecules of the Grignard reagent to each other, biphenyl derivatives can be produced more efficiently and with high productivity.

DETAILED DESCRIPTION

The processes for the production of biphenyl derivatives take the benzene derivative represented by the following general formula (2) as the starting substrate.

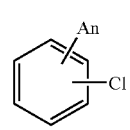

(wherein A represents, at least one member selected from the group consisting of trifluoromethyl and fluoro, and n is an integer of 1 to 4.)

In the above formula (2), n is an integer of 1 to 4, preferably 1. When n is 1, a more inexpensive substrate can be used, and since the substituent's function to sterically inhibit the reaction is slight, so that the reaction can proceed more efficiently.

Concrete examples of the starting substrate may include: o-chlorobenzotrifluoride, m-chlorobenzotrifluoride, p-chlorobenzotrifluoride, di(trifluoromethyl)-chlorobenzene, tri(trifluoromethyl)-chlorobenzene, tetra(trifluoromethyl)-chlorobenzene, o-chloro-fluorobenzene, m-chloro-fluorobenzene, p-chloro-fluorobenzene, chloro-difluorobenzene, chloro-trifluorobenzene, and chloro-tetrafluorobenzene, and the like. Among these, o-chlorobenzotrifluoride, m-chlorobenzotrifluoride, p-chlorobenzotrifluoride, o-chloro-fluorobenzene, m-chloro-fluorobenzene, and p-chloro-fluorobenzene are preferable.

The chlorine atom of the benzene derivative represented by the above formula (2) is made to react with metallic magnesium; thus forming a Grignard reagent. The formation reaction to the Grignard reagent is not particularly limited, and well known formation reactions can be used.

The form of the metallic magnesium is not particularly limited, but it is preferable to use a powdered form of the metal.

The reaction forming the Grignard reagent is conducted under anhydrous conditions in the system. It is preferable to remove water by using an anhydrous solvent or by adding an inexpensive Grignard reagent.

In addition; it is beneficial to add iodine, bromine, or inexpensive compounds including these to remove the surface oxide layer of the metallic magnesium and increase; reactivity. Preferable examples of these types of compounds include: methyl iodide, methyl bromide, ethyl iodide, ethyl bromide, and the like.

The catalyst used in the coupling reaction between two molecules of the Grignard reagent is preferably the metal Fe, Ag, Cu, Co, Zn, Ni, or Pd, or compounds thereof. Preferable compounds that may be used include: chlorides, bromides, iodides, fluorides, acetate salts, acetylacetonato salts, carbonates, hydroxides, and nitrates of the above metals. Among these, ferrous chloride (II), ferric chloride (III), ferrous bromide, and ferric bromide are preferable.

In addition, the quantity of catalyst used is preferably 0.01 mol % to 20 mol % with respect to the starting substrate, and more preferably 0.05 mol % to 10 mol %. By using a quantity of catalyst within the above ranges, the coupling reaction can be conducted efficiently and economically.

It is preferable to conduct the coupling reaction in the presence of an oxidizing agent. In the presence of the oxidizing agent, catalyst that has been reduced by the coupling reaction is easily oxidized and regenerated, thereby increasing the catalyst turnover number and improving reaction yield.

The substance used as the oxidizing agent is not particularly limited so long as it is capable of oxidizing metal. From the perspective of ease-of-use and separation from the product, halogenated aliphatic hydrocarbons are preferable, and halogenated aliphatic hydrocarbons with carbon numbers of 1 to 5 are more preferable. Specifically, this includes: chloromethane, dichloromethane, chloroform, carbon tetrachloride, bromomethane, dibromomethane; tribromomethane, tetrabromomethane, chloroethane, dichloroethane, trichloroethane, tetrachloroethane, tetrachloroethylene, pentachloroethane, hexachloroethane, bromoethane, dibromoethane, tribromoethane, tetrabromoethane, chloropropane, dichloropropane, trichloropropane, chlorobutane, dichlorobutane, chloropentane, dichloropentane, bromopropane, dibromopropane, tribromopropane, bromochloromethane, and bromochloroethane. Among these, chloromethane, dichloromethane, chloroethane, dichloroethane, dichloropropane, bromomethane, dibromomethane, bromoethane, dibromoethane, and dibromopropane are preferable, and dichloropropane is more preferable.

In addition, the quantity of oxidizing agent may preferably be a mole ratio of 0.1 to 5 with respect to 1 mole of the starting substrate, and more preferably the mole ratio of 0.2 to 3. When the quantity is less than the mole ratio of 0.1, the advantages of regenerating catalyst by the oxidizing agent are slight. When the quantity is greater than the mole ratio of 5, unreacted oxidizing agent remains and requires efforts to isolate and purify the target product, and thus it is inefficient.

The solvent used in the production process may be arbitrarily selected from any solvents that are capable of efficiently promoting the reaction. An ethereal solvent, wherein Grignard reagents are easily produced, is preferable. Concrete examples of solvents include: diethyl ether, diisopropyl ether, tetrahydrofuran, N,N-dimethylformamide, N,N-dimethylacetamide, N-methylpyrrolidone, 1,3-dioxane, 1,4-dioxane, cyclopropyl methyl ether, methyl tertiary butyl ether, ethylene glycol dimethyl ether, diethylene glycol dimethyl ether, methylene glycol dimethyl ether, tetraethylene glycol dimethyl ether, benzene, toluene, xylene, and the like. Among these, diethyl ether, diisopropyl ether, tetrahydrofuran, 1,3-dioxane, 1,4-dioxane, cyclopropyl methyl ether, and methyl tertiary butyl ether are preferable.

In addition, the quantity of solvent may be an arbitrary quantity chosen according to the solubility of the benzene derivative represented by the above formula (2), the Grignard reagent, and the product, the slurry concentration, or the characteristics of the reaction solution. Preferably, the mole ratio of solvent is 0.5 to 100 with respect to the benzene derivative represented by the above formula (2). When the mole ratio is less than 0.5, Grignard reagent yield is lowered, and when the mole ratio exceeds 100, productivity worsens and makes the process uneconomical.

The reaction temperature of the coupling reaction may preferably be 45° C. to 100° C., and even more preferably 55° C. to 70°G. When the reaction temperature is lower than 45° C., the reaction hardly proceeds at all, and even if the reaction does proceed, it may halt mid-reaction. Also, when the reaction temperature exceeds 100° C., the Grignard reagent may decompose before the reaction of producing biphenyl derivatives and thus such a temperature is not preferable.

During the coupling reaction in the production process, halogenated biphenyl derivatives represented by the following general formula (3) are generated as a by-product, in addition to the biphenyl derivatives, the target product of the invention, represented by the following general formula (1). Thus, compositions including biphenyl derivatives are obtained.

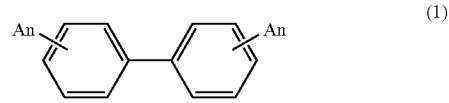

(1)

(wherein A represents at least one member selected from the group consisting of trifluoromethyl and fluoro, and n is an integer of 1 to 4.)

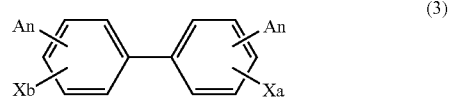

(3)

(wherein A represents at least one member selected from the group consisting of trifluoromethyl and fluoro, X represents halogen atoms, n is an integer of 1 to 4, a and b are integers, and the sum of a and b is 1 to 8.)

The compositions including biphenyl derivatives obtained by the production process preferably contain a quantity of the halogenated biphenyl derivatives represented by the above formula (3) that is 20 wt % or less, and more preferably 0.01 wt % to 20 wt %. A quantity of halogenated biphenyl derivatives exceeding 20 wt % leads to a lower-quality final product if the biphenyl derivatives are used as raw materials for such as fine chemicals, pharmaceuticals and agrichemicals, resins and plastics, electronic and information materials, and optical materials. More specifically, quality problems in the final product occur, such as lowered purity, coloration, lowered strength, and lowered optical characteristics, and as such is not preferable.

Consequently, in the production process, when there is a large quantity of halogenated biphenyl derivatives generated as a by-product, it is preferable to conduct separation and removal operations to reduce the quantity of halogenated as possible and isolate the target biphenyl derivatives. Preferable isolation methods include purification by distillation, crystallization, extraction, column separation using silica, simulated moving bed adsorption separation, and the like. Although any of these isolation methods may be used, purification by distillation is the most preferable among these. In addition, a plurality of these isolation methods may be used in combination to purify the product and further increase the purity thereof.

Since there is a possibility that active magnesium or other substances may remain in the reaction solution, it is preferable to conduct an isolation method wherein water or acidic water is added to the reaction solution, magnesium salts generated during the reaction are removed in the aqueous phase, and then the biphenyl derivatives are isolated from the obtained oil phase. The method of purification by distillation may involve simple distillation, rectification distillation, reduced-pressure distillation, or normal-pressure distillation, for example. Preferably, reduced-pressure distillation is used. In purification by distillation, since the halogenated biphenyl derivatives have a higher boiling point than the target biphenyl derivatives, it is necessary to perform distillation operations such that the biphenyl derivatives are distilled and the halogenated biphenyl derivatives are, as far as possible, not distilled and instead remain with the still residue.

The biphenyl derivatives obtained using one of the above isolation methods may contain a quantity of halogenated biphenyl derivatives that is preferably 0.01 wt % to 20 wt %, and more preferably 0.01 wt % to 5 wt %. By limiting the quantity of halogenated biphenyl derivatives to be within the above ranges, the quality in terms of purity, coloration, strength, optical characteristics, and the like of the final product using the biphenyl derivatives as a raw material can be maintained.

It is possible to convert the biphenyl derivatives obtained using the production process into a variety of compounds in a wide range of fields, and the fact that these biphenyl derivatives are obtainable inexpensively and in an industrially efficient manner is of great significance.

Hereinafter, our processes will be described in further detail with reference to examples. However, the processes are not to be limited to these examples.

Unless otherwise indicated, the chemical grades of the reagents used in the following examples and comparative example are equivalent to Grade 1 or higher.

Example 1

143.6 g tetrahydrofuran (1.99 mol; mfg. by Nacalai Tesque, Inc.) and 16.1 g magnesium powder (0.664 mol; mfg. by Chuo-Kosan Co., Ltd.) were put into a reactor with a temperature gauge and stirred while nitrogen substitution was conducted in the system. 2 g tertiary-butyl magnesium chloride (0.017 mol; mfg. by Tokyo Chemical Industry Co., Ltd.) was added, and water was removed from the system. Next, 10 g o-chlorobenzotrifluoride (0.0554 mol; mfg. by Miteni SpA) was put into the reactor, and subsequently, 2 g ethyl bromide (0.018 mol; mfg. by Nacalai Tesque, Inc.) was added. After a period of stirring, the presence of exothermic heat was confirmed. Next, 90 g o-chlorobenzotrifluoride (0.499 mol) was instilled while maintaining a reaction solution temperature of 35° C. to 50° C. After the completion of the instillation, the solution was aged while stirring for 3 hr at 45° C. Grignard reagent yield was 91%.

Next, a catalyst-containing solution was prepared by adding 65 g 1,2-dichloroethane (0.664 mol; mfg. by Nacalai Tesque, Inc.) to a mixture of 2.70 g iron chloride(III) (0.0166 mol; mfg. by Wako Pure Chemical Industries, Ltd.) and 3 g tetrahydrofuran (0.04 mol). Coupling reactions were conducted by instilling this solution into the above Grignard reagent solution while maintaining a reaction solution temperature of 45° C. to 60° C. After the completion of the instillation, reactions were conducted for 3 hr at 65° C. After the completion of the reactions, the reaction solution was cooled and then poured into water, the oil layer being extracted using diethyl ether (Special Grade; mfg. by Nacalai Tesque, Inc.). To this was added an internal reference substance, acetophenone (Special Grade; mfg. by Nacalai Tesque, Inc.). The solution was then analyzed using the gas chromatography method (column: InertCap 1, mfg. by GL Sciences Inc.; length 60 m×diameter 0.25 mm, thickness 0.40 μm). The yield of 2,2'-bis(trifluoromethyl) bi-phenyl with respect to o-chlorobenzotrifluoride was 69%. Also, the yield of chloro 2,2'-trifluoromethyl biphenyl as a by-product was 11 wt % with respect to 2,2'-bis(trifluoromethyl)biphenyl.

Example 2

Reactions identical to those of example 1 were conducted, with the exception of the catalyst being changed from iron chloride (III) to 5.86 g iron (III) acetylacetonate (0.0166 mol; mfg. by Wako Pure Chemical Industries, Ltd.). The yield of 2,2'-bis(trifluoromethyl)biphenyl with respect to o-chlorobenzotrifluoride was 48%. Also, the yield of chloro 2,2'-trifluoromethyl bi-phenyl as a by-product was 6.7 wt % with respect to 2,2'-bis(trifluoromethyl)biphenyl.

Example 3

Reactions identical to those of example 1 were conducted, with the exception of 1,2-dichloroethane being changed to 124.7 g 1,2-dibromoethane (0.664 mol; mfg. by Wako Pure Chemical Industries, Ltd.). The yield of 2,2'-trifluoromethyl biphenyl with respect to o-chloro-benzotrifluoride was 38%. Also, the yield of bromo 2,2'-trifluoromethyl biphenyl as a by-product was 29 wt % with respect to 2,2'-bis(trifluoromethyl)biphenyl.

Example 4

Reactions identical to those of example 1 were conducted, with the exception of 1,2-dichloroethane being changed to 75.0 g 1,2-dichloropropane (0.664 mol; mfg. by Wako Pure Chemical Industries, Ltd.). The yield of 2,2'-bis(trifluoromethyl)biphenyl with respect to o-chloro-benzotrifluoride was 72%. Also, the yield of chloro 2,2'-trifluoromethyl biphenyl as a by-product was 8.5 wt % with respect to 2,2'-bis(trifluoromethyl)biphenyl.

Example 5

A catalyst-containing solution was prepared by adding 75.0 g 1,2-dichloropropane (0.664 mol; mfg. by Wako Pure Chemical Industries, Ltd.) to a mixture of 2.70 g iron chloride (III) (0.0166 mol; mfg. by Wako Pure Chemical Industries, Ltd.) and 3 g tetrahydrofuran (0.04 mol). The Grignard reagent solution was then instilled into this catalyst-containing solution while maintaining a reaction solution temperature of 45° C. to 60° C. Other than the above, reactions identical to those of example 4 were conducted. The yield of 2,2'-bis(trifluoromethyl) bi-phenyl with respect to o-chlorobenzotrifluoride was 73%. Also, the yield of chloro 2,2'-trifluoromethyl biphenyl as a by-product was 1.7 wt % with respect to 2,2'-bis(trifluoromethyl)biphenyl.

Example 6

Reactions identical to those of example 1 were conducted, with the exception of o-chlorobenzotrifluoride being changed to m-chlorobenzotrifluoride (mfg. by Miteni SpA). The yield of 3,3'-bis(trifluoromethyl)biphenyl with respect to m-chlorobenzotrifluoride was 41%. Also, the yield of chloro 3,3'-trifluoromethyl biphenyl as a by-product was 10.5 wt % with respect to 3,3'-bis(trifluoromethyl)biphenyl.

Example 7

Reactions identical to those of example 4 were conducted, with the exception of the 10 g of o-chlorobenzotrifluoride being changed to 7.2 g p-chlorofluorobenzene (0.0554 mol; mfg. by Wako Pure Chemical Industries, Ltd.), as well as the 90 g of o-chlorobenzotrifluoride being changed to 65.2 g p-chlorofluorobenzene (0.499 mol; mfg: by Wako Pure Chemical Industries, Ltd.). The yield of 4,4'-difluoro biphenyl with respect to p-chlorofluorobenzene was 55%. Also, the yield of chloro 4,4'-difluoro biphenyl as a by-product was 3.5 wt % with respect to 4,4'-difluoro biphenyl.

Comparative Example 1

143.6 g tetrahydrofuran (1.99 mol; mfg. by Nacalai Tesque, Inc.) and 16.1 g magnesium powder (0.664 mol; mfg. by Chuo-Kosan Co., Ltd.) were put into a reactor with a temperature gauge and stirred while nitrogen substitution was conducted in the system. 2 g tertiary-butyl magnesium chloride (0.017 mol; mfg. by Tokyo Chemical Industry Co., Ltd.) was added, and water was removed from the system. Next, 10 g o-chlorobenzotrifluoride (0.0554 mol; mfg. by Miteni SpA) was put into the reactor, and subsequently, 2 g-ethyl bromide (0.018 mol; mfg. by Nacalai Tesque, Inc.) was added. After a period of stirring, the presence of exothermic heat was confirmed. Next, 90 g o-chlorobenzotrifluoride (0.499 mol) was, instilled while maintaining a reaction solution temperature of 35° C. to 50° C. After the completion of the instillation, the solution was aged while stirring for 3 hr at 45° C. Grignard reagent yield was 91%.

Example 7

Next, a solution of 3.59 g anhydrous nickel chloride (0.028 mol; mfg. by Nacalai Tesque, Inc.) dissolved into 30 g tetrahydrofuran was slowly put into the above Grignard reagent solution while maintaining a liquid temperature of 40° C. Next, 100 g o-chlorobenzotrifluoride was instilled while maintaining a reaction temperature of 60° C. After the completion of the reactions, the solution was analyzed similarly as in example 1 using the gas chromatography method. The yield of 2,2'-bis(trifluoromethyl)biphenyl with respect to o-chlorobenzotrifluoride was 2%. Also, the yield of chloro 2,2'-trifluoromethyl biphenyl as a by-product could not be discerned.

Example 8

100 g of the reaction solution obtained in example 1 was put into a 300 ml-size separatory funnel containing 100 g of 3% hydrochloric acid aqueous solution, thoroughly mixed for 30 min at room temperature, and rested for 30 min. After resting, 78.3 g of separated oil phase was obtained. Subsequently, this oil phase was simply distilled via reduced-pressure distillation. After the initial distillation cut, 17.3 g of distillate were obtained at 100° C. to 130° C. under a vacuum degree of 1.33 kPa. The concentration of 2,2'-bis(trifluoromethyl)biphenyl in the obtained distilled liquid was 95.6 wt %, and the concentration of chloro 2,2'-trifluoromethyl biphenyl was 3.5 wt %.

What is claimed is:

1. A process for producing biphenyl derivatives represented by formula (1), comprising:
    reacting a chlorine atom of a benzene derivative represented by formula (2) with metallic magnesium to form a Grignard reagent; and
    coupling two molecules of the Grignard reagent with each other in the presence of a catalyst comprising at least one metal or a compound thereof selected from the group consisting of Fe, Ag, Cu, Co, Zn and Pd

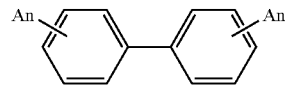

formula (1)

wherein A represents trifluoromethyl and n is an integer of 1 to 4

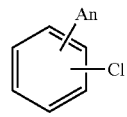

formula (2)

wherein A represents trifluoromethyl and n is an integer of 1 to 4.

2. The process according to claim 1, wherein the substituent A has a value of n equal to 1.

3. The process according to claim 1, wherein the coupling reaction is conducted in the presence of an oxidizing agent.

4. The process according to claim 3, wherein the oxidizing agent is a halogenated aliphatic hydrocarbon.

5. The process according to claim 1, wherein the reaction temperature of the coupling reaction is 45° C. to 100° C.

6. The process according to claim 1, wherein the biphenyl derivatives are purified by distillation, and wherein the content of halogenated biphenyl derivatives represented by the following general formula (3) is 0.01 wt % to 20 wt %

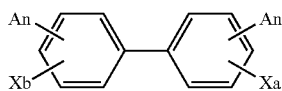

formula (3)

wherein A represents trifluoromethyl, X represents halogen atoms, n is an integer of 1 to 4, a and b are integers, and the sum of a and b is 1 to 8.

7. A biphenyl derivative composition, comprising:
biphenyl derivatives obtained by the process of claim 1; and
wherein the content of halogenated biphenyl derivatives represented by the following general formula (3) is 0.01 wt % to 20 wt %

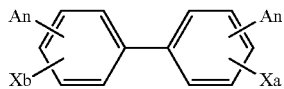

formula (3)

wherein A represents trifluoromethyl, X represents halogen atoms, n is an integer of 1 to 4, a and b are integers, and the sum of a and b is 1 to 8.

\* \* \* \* \*